United States Patent

Kwon et al.

[11] Patent Number: 5,804,700
[45] Date of Patent: Sep. 8, 1998

[54] DEVICE AND METHOD FOR SELF-DIAGNOSIS IN AIR-TO-FUEL RATIO SENSOR

[75] Inventors: Chang-soon Kwon, Sungnam; Chung-ho Lee, Seoul, both of Rep. of Korea

[73] Assignee: Samsung Electro-Mechanics Co., Ltd., Suwon, Rep. of Korea

[21] Appl. No.: 738,795

[22] Filed: Oct. 28, 1996

[30] Foreign Application Priority Data

Oct. 26, 1995 [KR] Rep. of Korea ............ 95-37451

[51] Int. Cl.$^6$ ............................................. G01N 27/26
[52] U.S. Cl. .................... 73/23.32; 73/1.06; 204/401; 204/427
[58] Field of Search ................... 73/23.2, 23.31, 73/23.32, 1.06, 1.07; 204/401, 424, 425, 422; 340/632; 205/782, 783.5

[56] References Cited

U.S. PATENT DOCUMENTS

| | | | |
|---|---|---|---|
| 4,819,602 | 4/1989 | Mieno et al. | 204/401 X |
| 4,938,194 | 7/1990 | Kato et al. | 204/401 X |
| 4,981,125 | 1/1991 | Kato et al. | 204/401 X |
| 5,047,137 | 9/1991 | Yamada et al. | 204/425 |
| 5,174,885 | 12/1992 | Hayakawa et al. | 204/425 |
| 5,265,458 | 11/1993 | Usami et al. | 73/23.32 |
| 5,558,752 | 9/1996 | Wang et al. | 204/401 |

*Primary Examiner*—Michael Brock
*Attorney, Agent, or Firm*—Burns, Doane, Swecker & Mathis, L.L.P.

[57] ABSTRACT

A device for self-diagnosis in a present invention includes a diffusion compartment having a porous diffusion passage at either end thereof, a sensing cell installed below the diffusion compartment for generating electromotive forces depending on the oxygen concentration via two electrodes provided on the upper and lower surfaces thereof, and a pumping cell for regulating the oxygen pressure in the diffusion compartment via two electrodes installed above the diffusion compartment. Also a method for self-diagnosis in a present invention comprises the step for operating A/F sensor, comparing a measured pumping voltage, making compensations in an output signal of the A/F sensor and diagnosing the corresponding A/F sensor if the pumping voltage value exceeds upper-limit voltage.

6 Claims, 5 Drawing Sheets

DEVICE AND METHOD FOR SELF-DIAGNOSIS IN AIR-TO-FUEL RATIO SENSOR

BACKGROUND OF THE INVENTION

The present invention relates to a method and device for self-diagnosis in an air-to-fuel ratio (A/F) sensor.

As air pollution due to exhausted gases from many kinds of vehicles becomes more serious, various efforts for preventing pollution have been performed. For example, the California Air Resource Board (CARB) in the U.S.A. has announced an on-board diagnosis (OBD) II which is capable of monitoring whether automobile parts which could influence on emission gases are operating abnormally. Though many related industrial companies continue to study various OBD methods, satisfactory effects have not yet been obtained.

The A/F sensor, a kind of a sensor for detecting the air-to-fuel ratio in the internal combustion engine, has been used particularly in lean burn engines developed for reducing the rate of fuel consumption. FIG. 1 is a schematic diagram showing the structure of a typical A/F sensor. As shown in FIG. 1, the A/F sensor includes a diffusion compartment 2 having a porous gas-diffusing passage 1 at either side thereof, a sensing cell 5 installed below the diffusion compartment 2, for generating electromotive forces depending on the oxygen concentration via two electrodes 3 and 4 provided at the upper and lower surfaces thereof, and a pumping cell 8 for regulating the oxygen partial pressure in the diffusion compartment 2 via two electrodes 6 and 7. Also, reference numeral 9 denotes a differential amplifier for driving the A/F sensor by receiving a sensing voltage generated in the sensing cell 5 and a predetermined reference voltage $V_{ref}$, and applying the output to the pumping cell 8. The component material of the sensing and pumping cells 5 and 8 is zirconium oxide ($ZrO_2$) having a certain conductivity of ion conduction. The operating principle of the A/F sensor as shown in FIG. 1 can be summarized as follows. The A/F sensor operates the pumping cell 8 to preserve the sensing voltage generated in the sensing cell 5 to a predetermined voltage, e.g., 0.45 V, and simultaneously measures the oxygen concentration in accordance with a pumping current $I_P$ in the pumping cell 8.

It is known that the characteristic degradation of the A/F sensor becomes more serious when operated in a fuel rich environment, which results from a blackening phenomenon in the component material, clogs in the diffusion passage and etc. The A/F sensor is known to more seriously be degraded in the characteristics than an λ sensor. However, the OBD method of A/F sensor has not been developed yet.

To diagnose the characteristic degradation of the A/F sensor, the corresponding A/F sensor should be separated from an engine and then diagnosed by utilizing a special diagnostic system or by using a reference gas or some other system. Therefore, it was very difficult and troublesome to measure the degradation of A/F sensor, the characteristics of the degraded A/F sensor could not be compensated correctly. Accordingly, precision and accuracy of a combustion control system was relatively low, which made an economical control of the engine increased harmful emission gases.

SUMMARY OF THE INVENTION

To solve the above problems, it is an object of the present invention to provide an on-board diagnosis (OBD) method and device for self-diagnosis in an air-to-fuel ratio (A/F) sensor, which can prolong life time of the A/F sensor, and also improve precision and accuracy of a combustion control system, to thereby prevent air pollution from exhausted gases.

To accomplish the above object, there is provided a method for self-diagnosis in an A/F sensor, comprising the steps of: operating said A/F sensor until the pumping current becomes a specific value and measuring the pumping voltage at that time; comparing a measured pumping voltage with a predetermined reference voltage and an upper-limit voltage; making compensations in the A/F sensor, if the pumping voltage is greater than said reference voltage and less than said upper-limit voltage; and diagnosing the corresponding A/F sensor to be "out of order", if the pumping voltage value exceeds said upper-limit voltage.

To accomplish the above object, there is provided a device for self-diagnosis in an A/F sensor, comprising: means for measuring a pumping voltage of an operating A/F sensor; and means for comparing the measured pumping voltage with a predetermined reference voltage, and an upper-limit voltage, and diagnosing the degradation state of the corresponding A/F sensor.

BRIEF DESCRIPTION OF THE DRAWINGS

The above object and advantage of the present invention will become more apparent by describing in detail a preferred embodiment thereof with reference to the attached drawings in which.

DETAILED DESCRIPTION OF THE INVENTION

Figure 1:
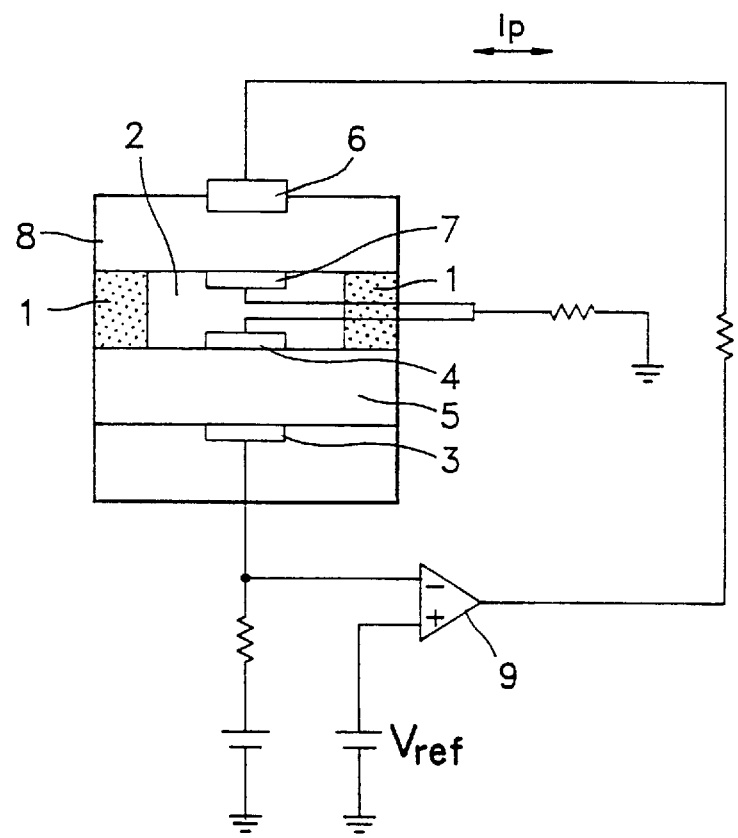
FIG. 1 is a schematic diagram showing the structure of a general air-to-fuel ratio (A/F) sensor.
Figure 2:
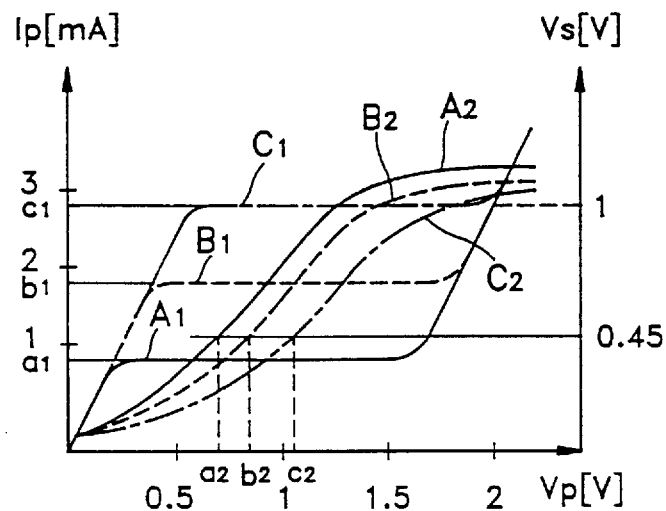
FIG. 2 shows characteristics of the pumping current and sensing voltage with respect to pumping voltage of the A/F sensor in a normal state.

Referring to FIG. 2, A1 denotes a characteristic curve of the pumping current $I_P$ with respect to a pumping voltage $V_P$ at the first oxygen concentration, A2 denotes a characteristic curve of a sensing voltage $V_S$ with respect to the pumping voltage $V_P$ at the first oxygen concentration, B1 denotes a characteristic curve of the pumping current $I_P$ with respect to the pumping voltage $V_P$ at the second oxygen concentration, B2 denotes a characteristic curve of the sensing voltage $V_S$ with respect to the pumping voltage $V_P$ at the second oxygen concentration, C1 denotes a characteristic curve of the pumping current $I_P$ with respect to the pumping voltage $V_P$ at the third oxygen concentration, and C2 denotes a characteristic curve of the sensing voltage $V_S$, with respect to the pumping voltage $V_P$ at the third oxygen concentration. Here, the second oxygen concentration is higher than the first, and the third is higher than the second. The general A/F sensor operates a pumping cell 8 of FIG. 1 to maintain the sensing voltage $V_S$ at a predetermined level, e.g., 0.45 V, and at the same time measures the oxygen concentration in accordance with the values of the pumping current $I_P$. As shown in FIG. 2, as the pumping current $I_P$ increases from $a_1$, to $b_1$, to $c_1$, the oxygen concentration increases accordingly. Thus, the pumping voltage $V_P$ increases from $a_2$, to $b_2$, to $c_2$ to keep the sensing voltage $V_S$ at 0.45 V.

Figure 3:
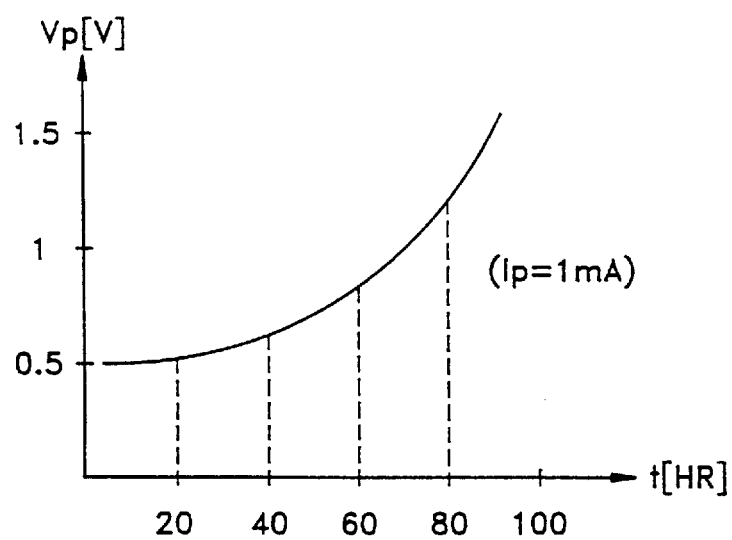
FIG. 3 shows characteristics of the pumping voltage with respect to degrading time of the general A/F sensor.

FIG. 3 shows an experimental result obtained from the degraded A/F sensor in a fuel rich environment. Here, with the oxygen concentration and the pumping current ($I_p$=1mA) are kept constant, the pumping voltage $V_P$ is measured with respect to degrading time, i.e., the operating time of A/F sensor in fuel rich condition for degradation. As can be seen, even with same oxygen concentration, the pumping voltage $V_P$ increases with degrading time. The present invention employs the characteristic of FIG. 3, that is, even with constant pumping currents $I_P$, the pumping voltage $V_P$ is proportional to degree of the degradation.

Figure 4:
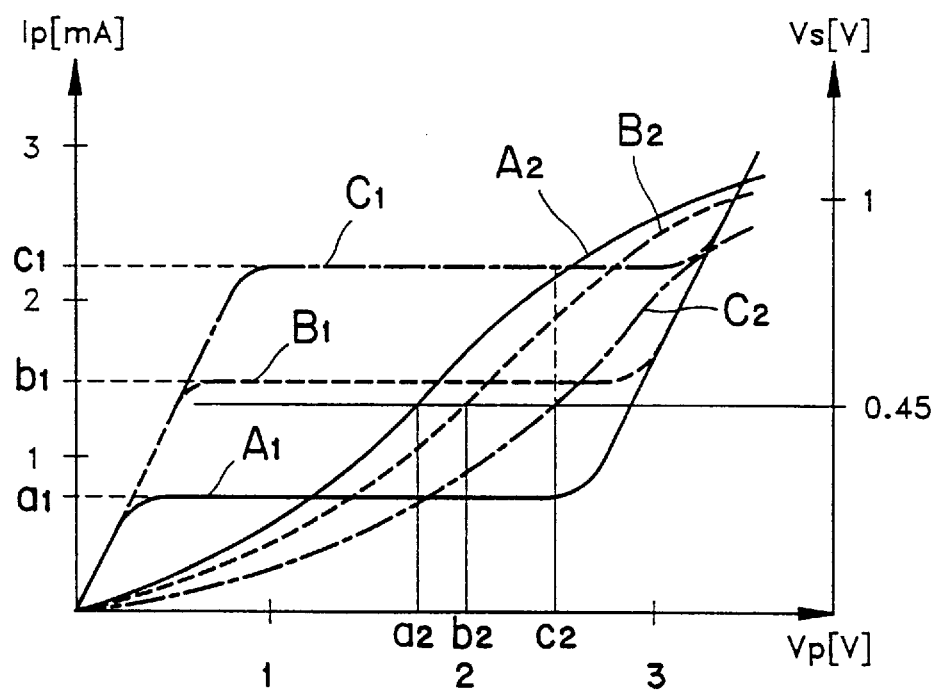
FIG. 4 shows characteristics of the pumping current and sensing voltage with respect to pumping voltage of the A/F sensor in a degraded state.

Compared to FIG. 2, the pumping voltage $V_P$ of FIG. 4 increases respectively and the pumping current $I_P$ of FIG. 4 decreases respectively at the same oxygen concentrations. Thus, the pumping voltage $V_P$ with respect to the pumping current $I_P$ is monitored like the characteristics in FIG. 4, so that the state of the corresponding A/F sensor can be diagnosed and such that follow-up measures can be taken. For example, if the pumping voltage $V_P$ is between a predetermined reference voltage and a predetermined upper-limit voltage, a microcomputer changes the pumping current $I_P$ into the correct value according to a conversion table. Also, if the pumping voltage $V_P$ exceeds the upper-limit voltage, the microcomputer sends a message for display and generates an alarm signifying failure of the corresponding A/F sensor.

Figure 5:
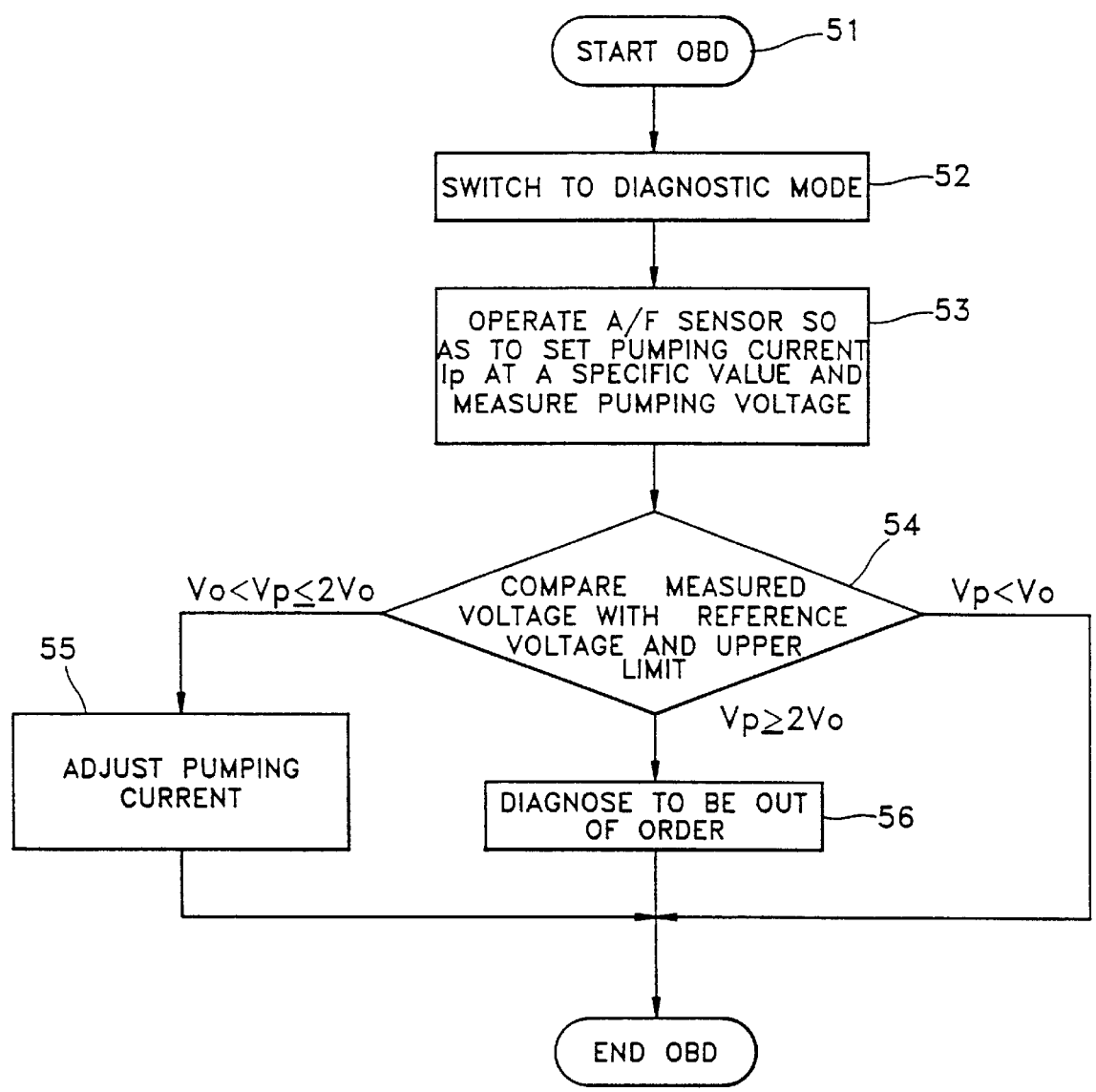
FIG. 5 is a flowchart illustrating a method for self-diagnosis in an A/F sensor according to the present invention.

Referring to FIG. 5, OBD designates an algorithm for detecting whether automobile parts influencing on the exhausted gases of a car operated normally or not. That is, the method for self-diagnosis in an A/F sensor according to the present embodiment can be conducted by being added to the OBD being applied. If the OBD is begun (step 51), the mode of operation of the A/F sensor is switched from a normal mode to a diagnosis mode (step 52). After the A/F sensor is operated SO that the pumping current $I_P$ reaches a specific level $I_O$ and the pumping voltage $V_P$ at that time is measured (step 53), the measured voltage $V_P$ is compared with a predetermined reference voltage and an upper-limit voltage (step 54). At this time, the reference voltage $V_0$ is determined as 1.2 times of an initial pumping voltage of the fresh sensor when pumping current $I_P$ is maintained at the specific value $I_0$. And the upper-limit voltage is determined as twice the reference voltage, that is, 2 $V_0$. The reference voltages i.e., the low and upper limit voltage are kept in the microcomputer. Then, if the measured pumping voltage $V_P$ falls below the reference voltage $V_0$, the characteristics of the A/F sensor is diagnosed as "good." However, if the measured pumping voltage $V_P$ is between the reference voltage $V_0$ and upper-limit voltage 2 $V_0$, compensation adjustments are made to the corresponding A/F sensor by utilizing the conversion table between the measured pumping current and the compensation current in the microcomputer (step 55). Also, if the measured pumping voltage $V_P$ exceeds the upper-limit voltage 2 $V_0$, the corresponding A/F sensor is diagnosed to be out of order (step 56). This disorder diagnosis involves the actions of, for example, displaying the failure of the corresponding A/F sensor, generating a warning sound, or lighting a warning lamp, and disregaring signals from the out-of-order A/F sensor, thereby preventing malfunction of the system.

Figure 6:
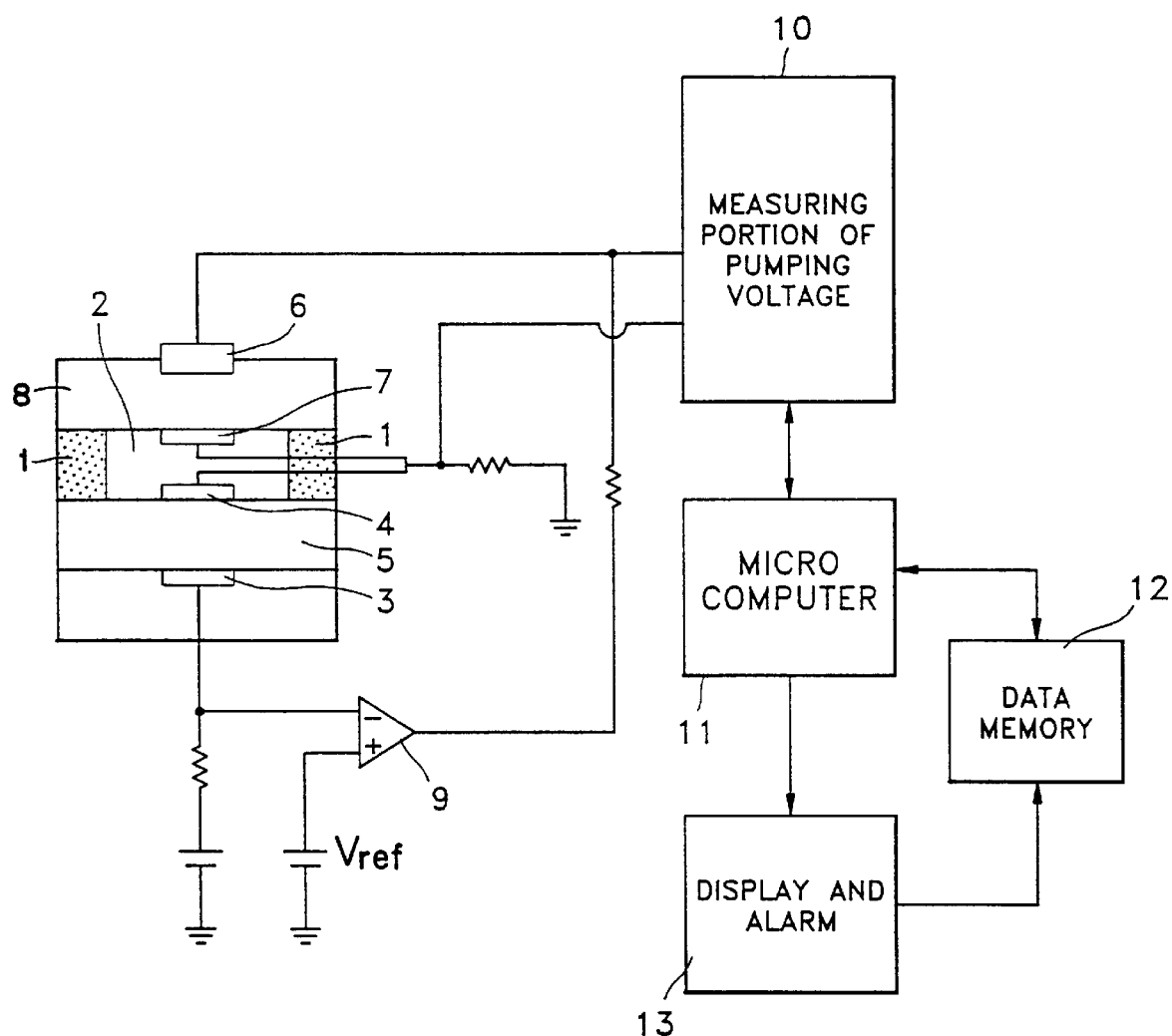
FIG. 6 is a schematic diagram showing the structure of a device for self-diagnosis in an A/F sensor according to the present invention.

Referring to FIG. 6, the general A/F sensor includes a diffusion compartment 2 having a porous diffusion passage 1 at either end thereof, a sensing cell 5 installed below the diffusion compartment 2 for generating electromotive forces depending on the oxygen concentration via two electrodes 3 and 4 provided on the upper and lower surfaces thereof, and a pumping cell 8 for regulating the oxygen pressure in the diffusion compartment 2 via two electrodes 6 and 7, installed above the diffusion compartment 2. Also, reference numeral 9 denotes a differential amplifier for driving the A/F sensor by receiving a sensing voltage generated in the sensing cell 5 and a predetermined reference voltage $V_{ref}$, and applying the output to the pumping cell 8.

Hereinbelow, the structure and operation of the device for self-diagnosis according to the present invention will be described with reference to FIG. 6. A pumping voltage measuring portion 10 measures the pumping voltage $V_P$, and then outputs the measured pumping voltage $V_P$ into a microcomputer 11. The microcomputer 11 compares the input pumping voltage $V_P$ with a predetermined reference voltage $V_0$ and an upper-limit voltage 2 $V_0$ stored in a data memory 12 via a self-diagnosis algorithm stored in the microcomputer 11. Here, the data stored in the data memory 12 can be regulated according to characteristics of A/F sensors and systems to be applied. After the comparison, if the measured pumping voltage $V_P$ falls below the reference voltage $V_0$, the characteristics of the corresponding A/F sensor is diagnosed as "good". However, if the measured pumping voltage $V_P$ is between the reference voltage $V_0$ and the upper-limit voltage 2 $V_0$, the pumping current $I_P$ of A/F sensor is compensated into the correct value according to the conversion table in the microcomputer. Also, if the measured pumping voltage $V_P$ exceeds the upper-limit voltage 2 $V_0$, the corresponding A/F sensor is diagnosed to be "out of order". At this time, a display and alarm 13 displays the failure of the corresponding A/F sensor, and generates a warning sound or lights a warning lamp. Here, the action of the display and alarm 13 is additionally stored in the data memory 12.

As described above, this invention could monitor and detect easily the mulfunction of A/F sensor which is mounted in the internal combustion system. This invention prevents producing the harmful exhaust gases by the malfunction of A/F sensor in the combustion engine. This invention could compensate the small degradation in the characteristics of A/F sensor. Therefore, it could lengthen the life time of the A/F sensor.

The present invention is not limited to the above embodiment, and various changes and improvements may be effected by those skilled in the art.

What is claimed is:

1. A method for self-diagnosis in an A/F sensor comprising the step of:

operating said A/F sensor so that a pumping current reaches at a specific level and measuring a pumping voltage when the pumping current reaches the specific level;

comparing the pumping voltage obtained when the pumping current reaches the specific level with a predetermined reference voltage and an upper-limit voltage;

making compensations in an output of the A/F sensor, if the pumping voltage is greater than the reference voltage and less than the upper-limit voltage; and diagnosing the corresponding A/F sensor to be misfunctioning, if the pumping voltage value exceeds the upper-limit voltage.

2. A device for self-diagnosis in an A/F sensor, comprising:

means for measuring a pumping voltage of an operating A/F sensor; and means for comparing the measured pumping voltage with a predetermined reference voltage, and an upper-limit voltage, and diagnosing the degradation state of the corresponding A/F sensor.

3. A device for self-diagnosis in an A/F sensor as claimed in claim 2, wherein said comparing and diagnosing means is a microcomputer having a predetermined self-diagnosis algorithm stored therein.

4. A device for self-diagnosis in an A/F sensor as claimed in claim 2, further comprising:

a data memory for storing said reference voltage, said upper-limit voltage, and related data.

5. An A/F sensor comprising:

a diffusion compartment having a porous diffusion passage;

a sensing cell adjacent the diffusion compartment for generating electromotive forces, depending on the oxygen concentration in the diffusion compartment, via electrodes provided on upper and lower surfaces of the sensing cell;

a pumping cell for regulating the oxygen pressure in the diffusion compartment via electrodes adjacent the diffusion compartment;

means for measuring the pumping voltage of the pumping cell;

means for comparing the measured pumping voltage with a predetermined reference voltage, and an upper-limit voltage, and diagnosing the degradation state of the corresponding A/f sensor.

6. An A/F sensor as claimed in claim 5, further comprising:

a data memory for storing said reference voltage, said upper-limit voltage, and related data.

* * * * *